United States Patent
Ito

(10) Patent No.: US 10,449,070 B2
(45) Date of Patent: Oct. 22, 2019

(54) NANOPARTICLES AND NANOPARTICLE COMPOSITION, AND METHOD FOR PRODUCING NANOPARTICLES AND NANOPARTICLE COMPOSITION

(71) Applicants: KINKI UNIVERSITY, Higashiosaka-shi, Osaka (JP); OTSUKA PHARMACEUTICAL CO., LTD., Tokyo (JP)

(72) Inventor: Yoshimasa Ito, Higashiosaka (JP)

(73) Assignees: Kinki University, Osaka (JP); OTSUKA PHARMACEUTICAL CO., LTD., Tokyo (JP)

(*) Notice: Subject to any disclaimer, the term of this patent is extended or adjusted under 35 U.S.C. 154(b) by 0 days.

(21) Appl. No.: 14/910,170

(22) PCT Filed: Aug. 7, 2014

(86) PCT No.: PCT/JP2014/070841
§ 371 (c)(1),
(2) Date: Feb. 4, 2016

(87) PCT Pub. No.: WO2015/020139
PCT Pub. Date: Feb. 12, 2015

(65) Prior Publication Data
US 2016/0175127 A1    Jun. 23, 2016

(30) Foreign Application Priority Data
Aug. 7, 2013    (JP) .................. 2013-163895

(51) Int. Cl.
*A61K 9/00*    (2006.01)
*A61F 2/94*    (2013.01)
(Continued)

(52) U.S. Cl.
CPC .............. *A61F 2/94* (2013.01); *A61K 9/146* (2013.01); *A61K 31/196* (2013.01);
(Continued)

(58) Field of Classification Search
CPC ........................................... A61F 2/94
See application file for complete search history.

(56) References Cited

U.S. PATENT DOCUMENTS

2005/0033414 A1    2/2005    Zhang et al.
2005/0043788 A1    2/2005    Luo et al.
(Continued)

FOREIGN PATENT DOCUMENTS

AU    2013 206 706 A1    7/2013
CN        1552474 A    12/2004
(Continued)

OTHER PUBLICATIONS

Elaine Merisko-Liversidge, Nanosizing: a formulation approach for poorly-water-soluble compounds, European Journal of Pharmaceutical Sciences, 2003, 18, 133-120.*

(Continued)

*Primary Examiner* — Paul W Dickinson
(74) *Attorney, Agent, or Firm* — Sughrue Mion, PLLC

(57) ABSTRACT

The present invention relates to a nanoparticle composition which is prepared by a process which is characterized by dissolving a poorly water-soluble compound or the like under a high temperature and a high pressure, and milling a suspension or the like containing a uniform crystal obtained by cooling the obtained solution.

13 Claims, 8 Drawing Sheets

CLZ bulk powder

CLZ bulk powder after levigation

(51) Int. Cl.
| | |
|---|---|
| A61K 47/24 | (2006.01) |
| A61K 47/38 | (2006.01) |
| A61K 47/40 | (2006.01) |
| A61K 31/405 | (2006.01) |
| A61K 31/4709 | (2006.01) |
| A61K 31/196 | (2006.01) |
| A61L 29/16 | (2006.01) |
| A61L 31/16 | (2006.01) |
| A61L 24/00 | (2006.01) |
| A61K 9/14 | (2006.01) |
| A61L 29/08 | (2006.01) |
| A61L 31/08 | (2006.01) |
| A61M 25/10 | (2013.01) |
| B82Y 5/00 | (2011.01) |
| B82Y 40/00 | (2011.01) |

(52) U.S. Cl.
CPC ........ *A61K 31/405* (2013.01); *A61K 31/4709* (2013.01); *A61K 47/24* (2013.01); *A61K 47/38* (2013.01); *A61K 47/40* (2013.01); *A61L 24/0015* (2013.01); *A61L 29/08* (2013.01); *A61L 29/16* (2013.01); *A61L 31/08* (2013.01); *A61L 31/16* (2013.01); *A61M 25/10* (2013.01); *A61F 2250/0067* (2013.01); *A61F 2310/0097* (2013.01); *A61L 2300/63* (2013.01); *A61L 2300/802* (2013.01); *A61L 2400/06* (2013.01); *A61L 2400/12* (2013.01); *B82Y 5/00* (2013.01); *B82Y 40/00* (2013.01)

(56) References Cited

U.S. PATENT DOCUMENTS

| | | |
|---|---|---|
| 2006/0073199 A1 | 4/2006 | Chaubal et al. |
| 2009/0297596 A1* | 12/2009 | Devane ................ A61K 9/2054 424/456 |
| 2012/0213838 A1 | 8/2012 | Egashira et al. |
| 2013/0035279 A1 | 2/2013 | Venkataraman et al. |

FOREIGN PATENT DOCUMENTS

| | | | |
|---|---|---|---|
| CN | 101287451 A | 10/2008 | |
| EP | 2 184 109 A1 | 5/2010 | |
| JP | 2003-531162 A | 10/2003 | |
| JP | 2006-028108 A | 2/2006 | |
| JP | 2007-215620 A | 8/2007 | |
| JP | 2008-519759 A | 6/2008 | |
| JP | 2009-082902 A | 4/2009 | |
| WO | 2001/080828 A2 | 11/2001 | |
| WO | WO 2005123033 A2 * | 12/2005 | ........... A61K 9/1688 |
| WO | 2006/052018 A1 | 5/2006 | |
| WO | 2007/129829 A1 | 11/2007 | |
| WO | 2008030209 A2 | 3/2008 | |
| WO | 2009/017259 A1 | 2/2009 | |
| WO | 2011/024831 A1 | 3/2011 | |

OTHER PUBLICATIONS

Extended European Search Report dated Feb. 7, 2017, from the European Patent Office in counterpart European Application No. 14835114.1.
Miao, Xiaoqing, et al., "Investigation of Nanosized Crystalline Form to Improve the Oral Bioavailability of Poorly Water Soluble Cilostazol", Journal of Pharmacy and Pharmaceutical Sciences, vol. 14, No. 2, Jan. 1, 2011, pp. 196-214, XP055337321.
Jeon, Doo-Soo, et al., "The Effect of Cilostazol on Stent Thrombosis After Drug-Eluting Stent Implantation", Korean Circulation Journal, vol. 40, No. 1, Jan. 1, 2010, p. 10 (1 page), XP055339006.
Takayama, K., et al., "Effect of Cilostazol in Preventing Restenosis after Carotid Artery Stenting Using the Carotid Wallstent: A Multicenter Retrospective Study", American Journal of Neuroradiology, vol. 33, No. 11, Dec. 2012, pp. 2167-2170 (4 pages), XP055339007.
Jeon, D.-S.., et al., "The Effect of Cilostazol on Stent Thrombosis After Drug-Eluting Stent Implantation", Korean Circulation Journal, vol. 40, No. 1, Jan. 1, 2010, pp. 10-15 (6 pages).
Ito et al., "Preparation of Ophthalmic Formulations Containing Drug Nanoparticles and its Applicability: Corneal Permeability of the Ophthalmic Formulations", Japan Cornea Society Sokai Keratoplasty Society of Japan Program Shorokushu, Feb. 2013, vol. 29-37, p. 107 (P068) (2 pages total).
Murao et al., "Therapeutic Effect of Formulations containing Cilostazol Nanoparticles in Cerebral Ischemia Model Rats", Abstracts of the 131st Annual Meeting of Pharmaceutical Society of Japan, Apr. 2011, p. 189 (30H-am09) (2 pages total).
Yoshioka et al., "Evaluation of Usefulness in OD tablets containing Cilostazol Nanoparticles", Abstracts of the 132nd Annual Meeting of Pharmaceutical Society of Japan, Apr. 2012, p. 318 (31P2-pm141) (2 pages total).
Ito et al., "Improvement of Transcorneal Penetration of Cilostazol by Its Nano Particle," Abstracts of the 129th Annual Meeting of Pharmaceutical Society of Japan, Apr. 2009, p. 186 (26P-pm010) (2 pages total).
Fujimura, "Enhancement of drug exposure by nanosized formulation for poorly water-soluble compounds-usefulness in toxicity studies", The Journal of Toxicological Sciences, 2012, vol. 37, No. Supplement I, p. S264 (P-215) (2 pages total).
Nagai and Ito, "A New Preparation Method for Ophthalmic Drug Nanoparticles", Pharmaceutica Analytica Acta, vol. 5, Issue 6, 1000305, 2014, pp. 1-4 (5 pages total).
Nagai et al., "A nanoparticle formulation reduces the corneal toxicity of indomethacin eye drops and enhances its corneal permeability", Toxicology, vol. 319 (2014) pp. 53-62 (10 pages total).
Nagai and Ito, "Effect of Solid Nanoparticle of Indomethacin on Therapy for Rheumatoid Arthritis in Adjuvant-Induced Arthritis Rat", Biological and Pharmaceutical Bulletin, 2014, vol. 37, No. 7, pp. 1109-1118 (10 pages total).
Nagai et al., "Improved Corneal Toxicity and Permeability of Tranilast by the Preparation of Opthalmic Formulations Containing its Nanoparticles", Journal of Oleo Science, ISSN 1345-8957, 2014, pp. 1-10 (10 pages total).
Nagai and Ito, "Therapeutic Effects of Gel Ointments Containing Tranilast Nanoparticles on Paw Edema in Adjuvant-Induced Arthritis Rats", Biological Pharmaceutical Bulletin, 2014, vol. 37, No. 1, pp. 96-104 (9 pages total).
International Search Report, issued by the International Searching Authority in corresponding Application No. PCT/JP2014/070841, dated Nov. 4, 2014.
International Preliminary Report on Patentability issued from the International Bureau in corresponding International Application No. PCT/JP2014/070841, dated Feb. 18, 2016.
Communication dated Aug. 28, 2018 from the European Patent Office in counterpart Application No. 14835114.1.
Jan P. Moschwitzer, "Drug nanocrystals in the commercial pharmaceutical development process", International Journal of Pharmaceutics vol. 453, 2013, pp. 142-156 (16 pages total).

* cited by examiner

[Fig. 1]
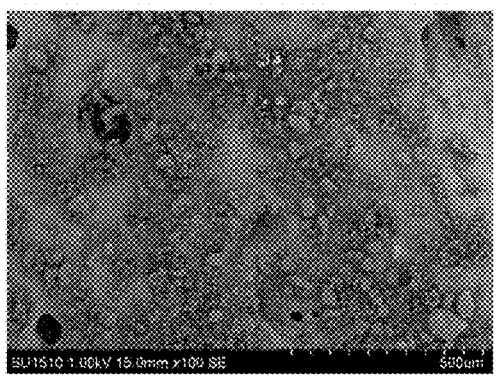
CLZ bulk powder
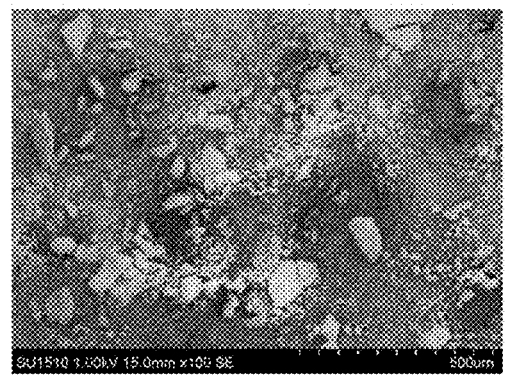
CLZ bulk powder after levigation
[Fig. 2]
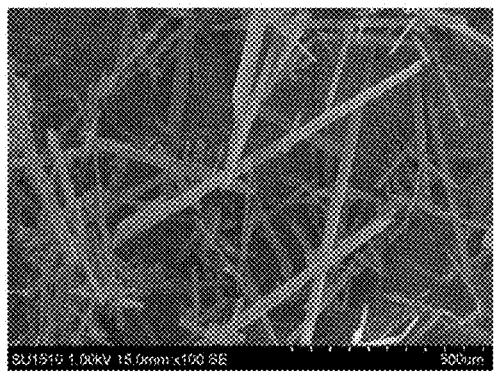
CLZ recrystal from water solvent
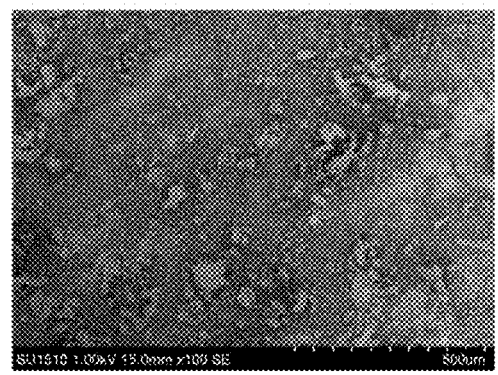
CLZ recrystal from water solvent after levigation
[Fig. 3]
CLZ recrystal from 50% ethanol solvent
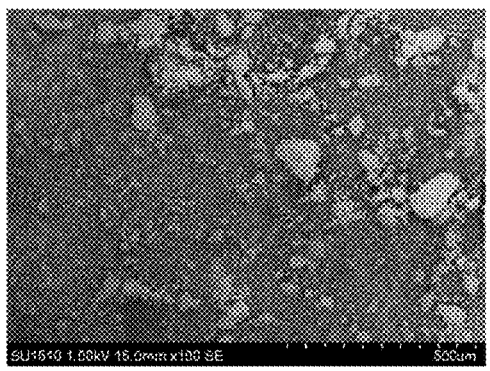
CLZ recrystal from 50% ethanol solvent after levigation

[Fig. 4]
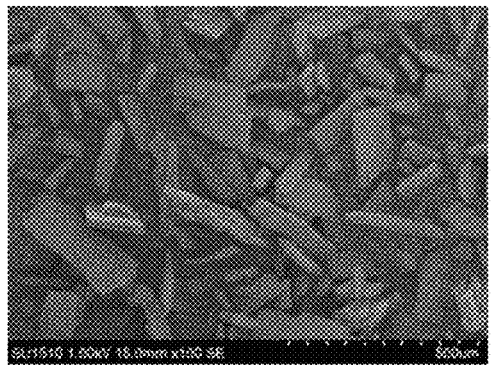
TRA bulk powder
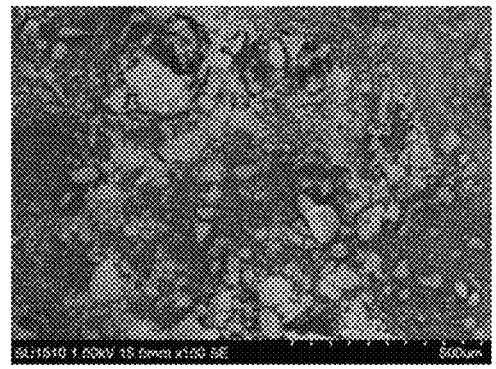
TRA bulk powder after levigation
[Fig. 5]
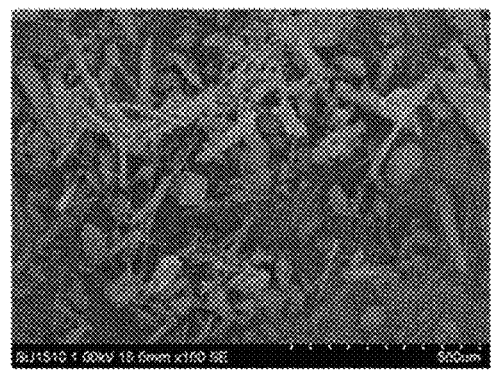
TRA recrystal from water solvent
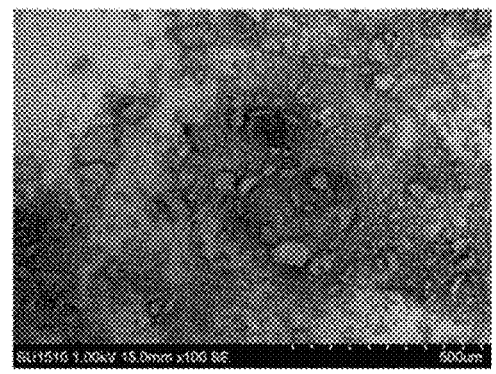
TRA recrystal from water solvent after levigation
[Fig. 6]
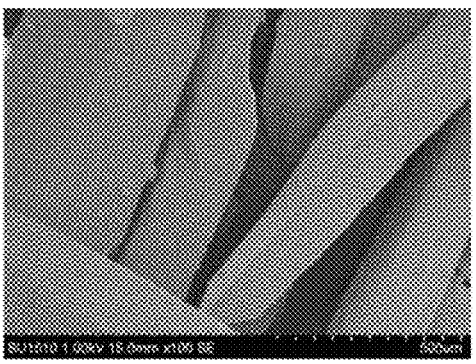
TRA recrystal from 50% ethanol solvent
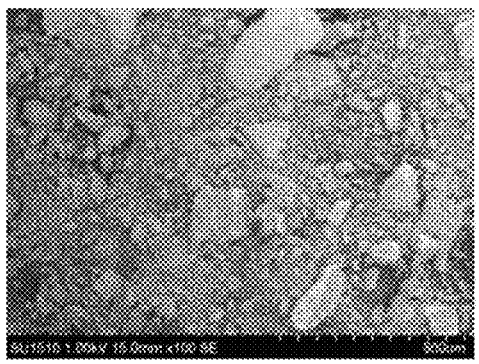
TRA recrystal from 50% ethanol solvent after levigation

[Fig. 7]
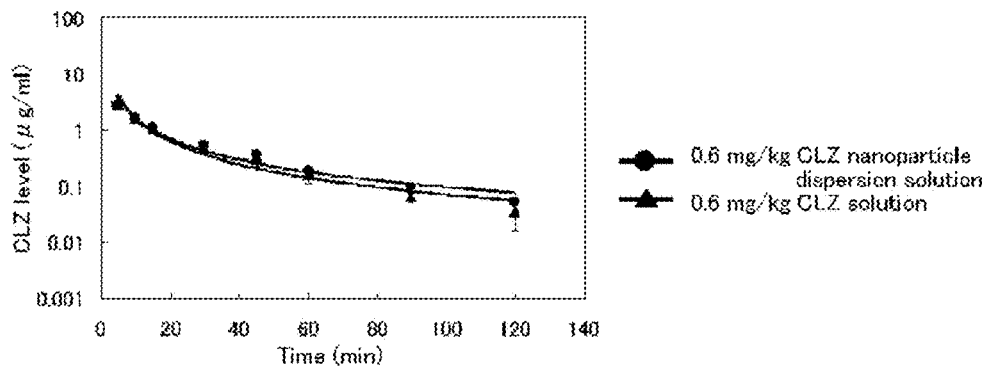
[Fig. 8]
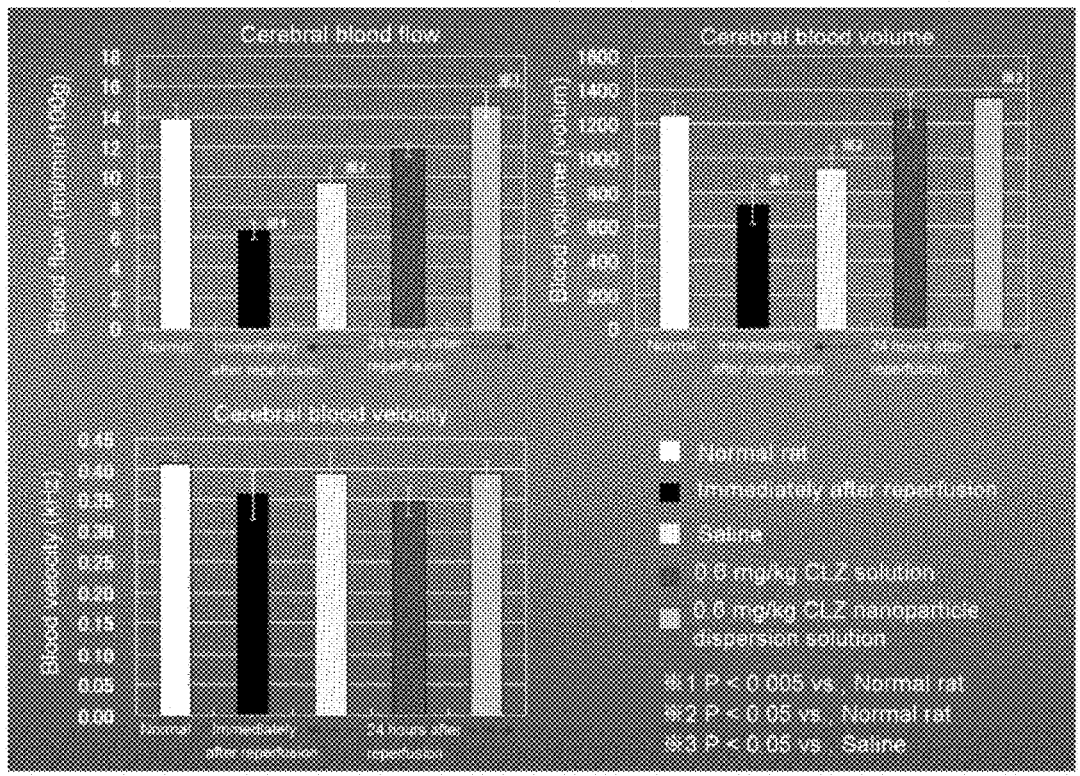

[Fig. 9]

| Rp. | Content (%) | | | | | | |
|---|---|---|---|---|---|---|---|
| | CLZ | HPC | Docu-Na | HPβCD | Carbopol 934 | PEG 400 | PEG 4000 |
| CLZ gel ointment | 0.5 | - | - | 5.0 | 1.5 | - | - |
| CLZ$_{nano}$ gel ointment | 0.5 | 0.01 | 0.005 | 5.0 | 1.5 | - | - |
| CLZ$_{nano}$ PEG ointment | 0.5 | 0.01 | 0.005 | 5.0 | - | 47.2 | 47.2 |

HPC: Hydroxypropyl cellulose
Docu-Na: Sodium di(2-ethylhexyl)sulfosuccinate
HPβCD: Hydroxypropyl-β-cyclodextrin

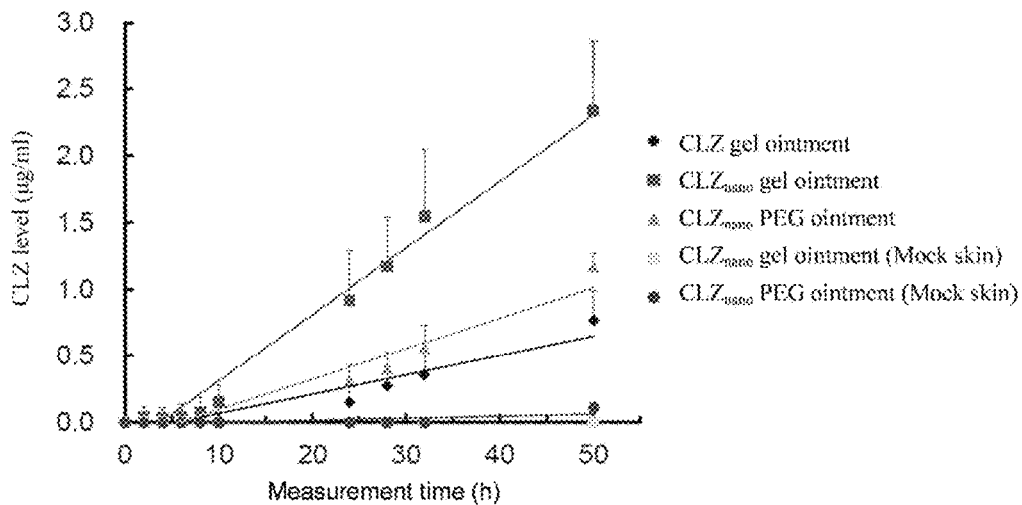

| Rp. | $J_i$ (ng/cm²/h) | $K_p$ (× 10⁻⁴ cm/h) | $K_{el}$ (× 10⁻³) | $\tau$ (h) | $D$ (× 10⁻⁴ cm²/h) |
|---|---|---|---|---|---|
| CLZ gel ointment | 104 ± 28.1 | 2.98 ± 0.83 | 13.7 ± 5.41 | 5.52 ± 1.95 | 1.83 ± 1.10 |
| CLZ$_{nano}$ gel ointment | 306 ± 67.4*¹,² | 8.76 ± 1.93 | 27.5 ± 13.4 | 3.75 ± 1.78 | 3.04 ± 2.33 |
| CLZ$_{nano}$ PEG ointment | 160 ± 11.8 | 4.58 ± 0.34 | 22.2 ± 0.92 | 5.75 ± 0.64 | 1.47 ± 0.16 |

*¹ $p < 0.005$, vs. CLZ gel ointment  *² $p < 0.05$, vs. CLZ$_{nano}$ PEG

[Fig. 12]
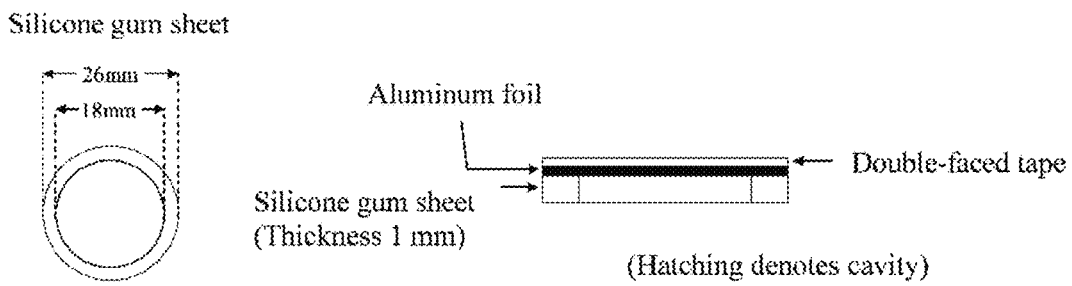
[Fig. 13]
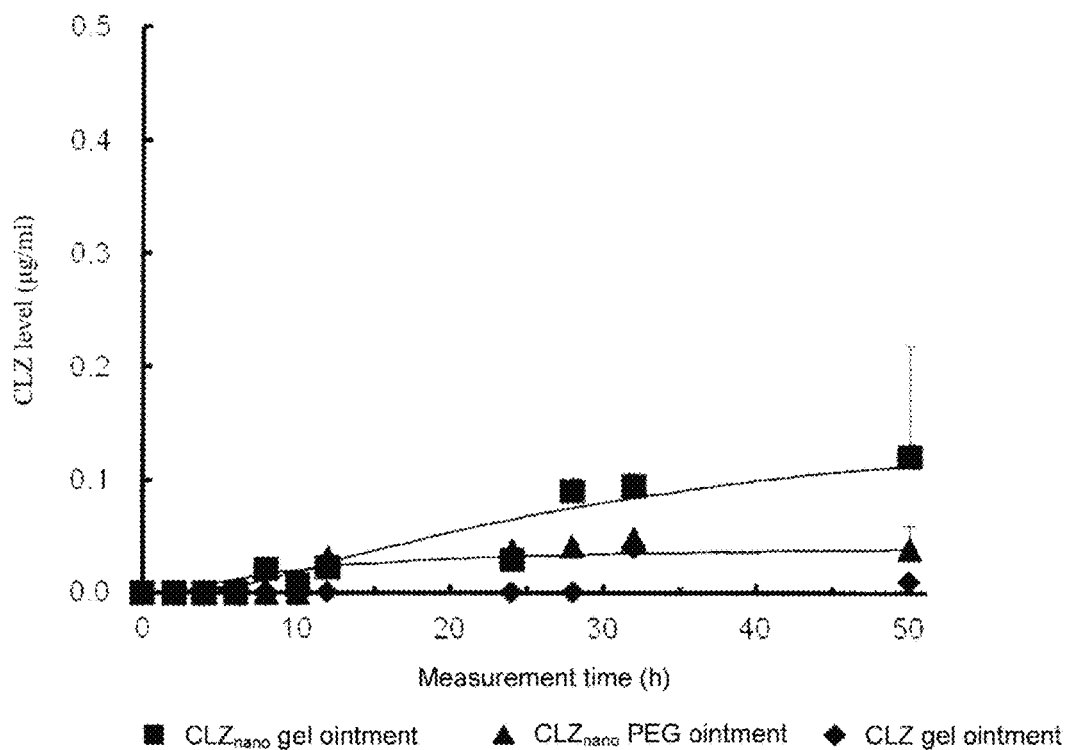

[Fig. 14]
$$C_p = \frac{A \cdot k_a}{k_a - \alpha} e^{-\alpha(t-\tau)} + \frac{B \cdot k_a}{k_a - \beta} e^{-\beta(t-\tau)} - \left( \frac{A \cdot k_a}{k_a - \alpha} + \frac{B \cdot k_a}{k_a - \beta} \right) e^{-k_a(t-\tau)}$$
α: 0.163 (from CLZ solution i.v. results)
β: 0.034 (from CLZ solution i.v. results)
| | $k_a$ (× 10⁻³/h) | A (μg/mL) | B (μg/mL) | τ (h) |
|---|---|---|---|---|
| CLZ_nano gel ointment | 11.7 ± 4.1[1,3] | 8.06 ± 1.14 | 4.99 ± 1.30 | 2.66 ± 1.09 |
| CLZ_nano PEG ointment | 7.1 ± 0.2[2,3] | 4.58 ± 0.28 | 3.81 ± 0.47 | 2.67 ± 0.55 |
| CLZ gel ointment | N.D. | N.D. | N.D. | N.D. |
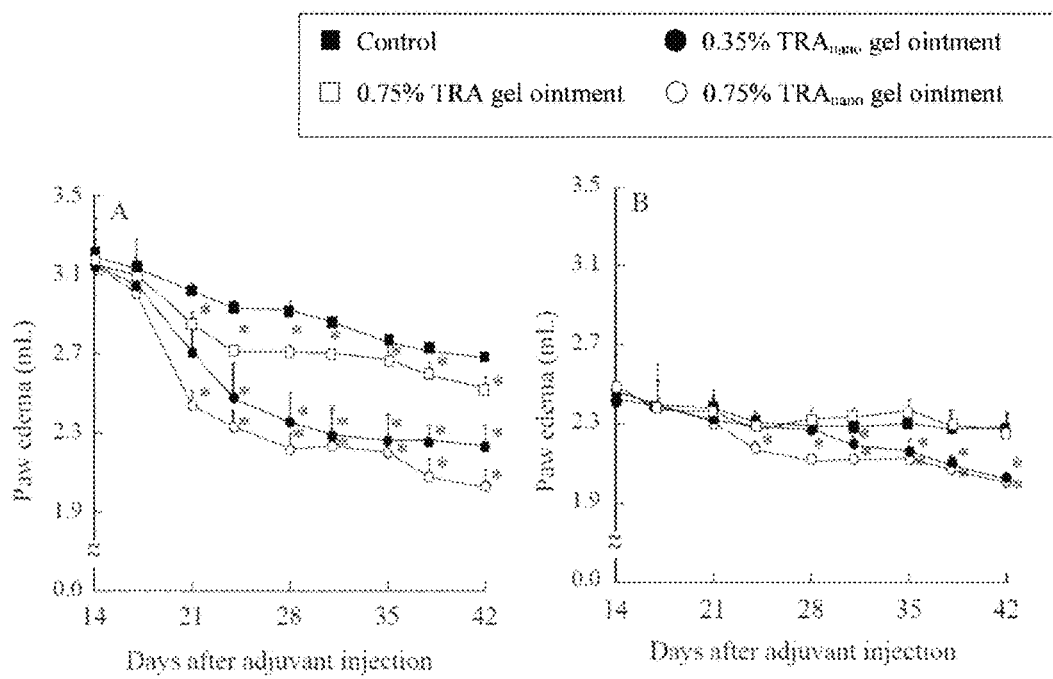
[Fig. 15]

[Fig. 16]
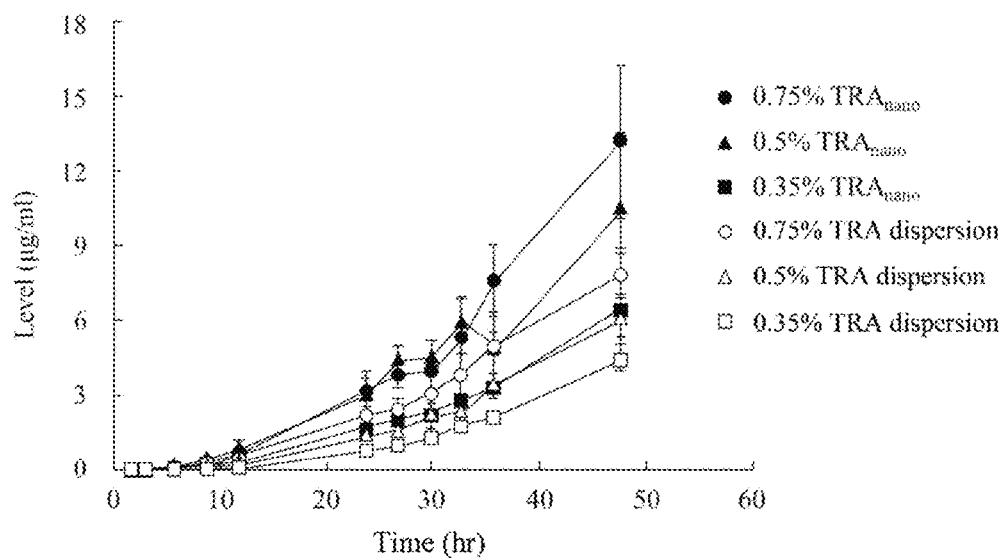
[Fig. 17]
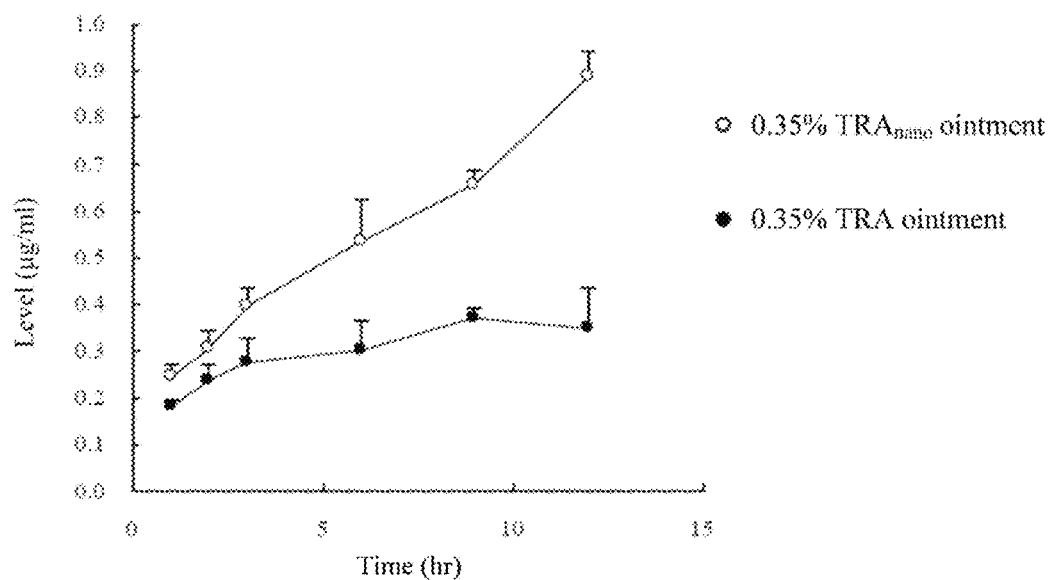

[Fig. 18]
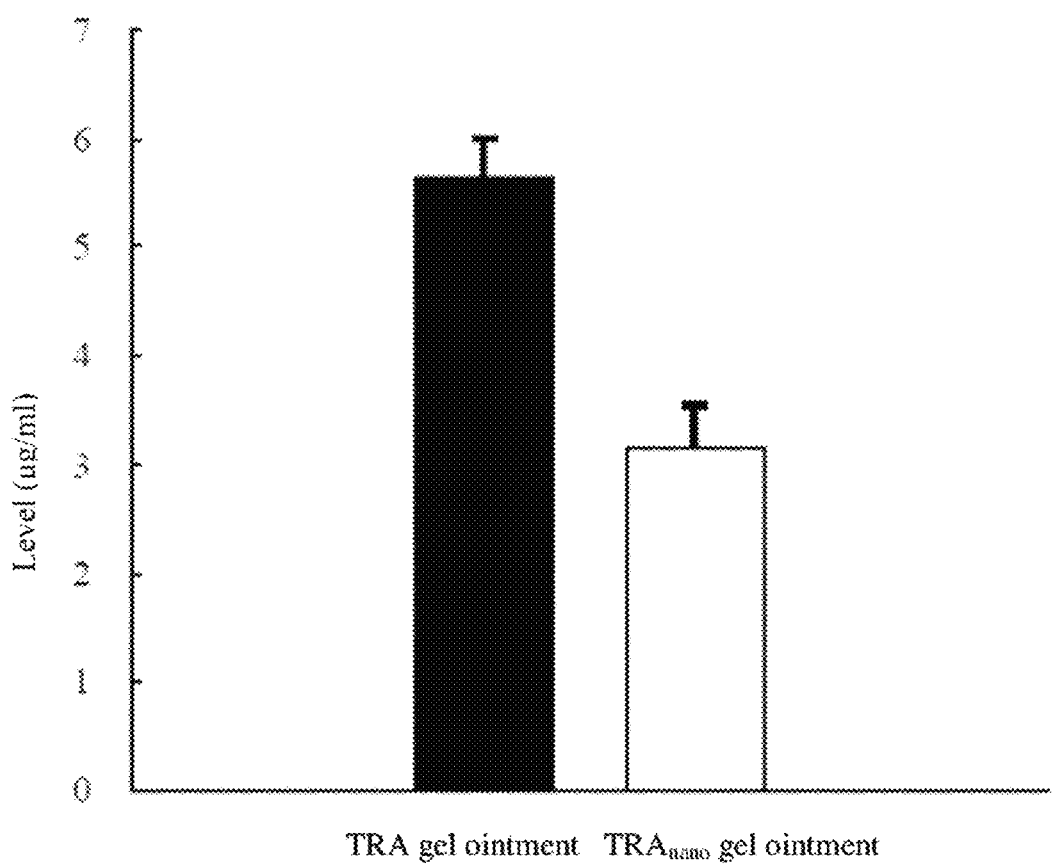

NANOPARTICLES AND NANOPARTICLE COMPOSITION, AND METHOD FOR PRODUCING NANOPARTICLES AND NANOPARTICLE COMPOSITION

CROSS REFERENCE TO RELATED APPLICATIONS

This application is a National Stage of International Application No. PCT/JP2014/070841 filed Aug. 7, 2014, claiming priority based on Japanese Patent Application No. 2013-163895 filed Aug. 7, 2013, the contents of all of which are incorporated herein by reference in their entirety.

TECHNICAL FIELD

The present invention relates to a method of preparing a nanoparticle of a medicinal product or a composition comprising a nanoparticle of a medicinal product in which said medicinal product is water-insoluble or poorly water-soluble; the nanoparticle; and the composition comprising the nanoparticle. In particular, it relates to a method comprising dissolving a water-insoluble or poorly water-soluble compound in water or the like at a high temperature and under a high pressure, cooling the resulting solution to give a suspension comprising a uniform crystal of the compound, or followed by isolation to give the isolated crystal, and milling the suspension or the isolated crystal; the nanoparticle which is obtained thereby; and a composition comprising the nanoparticle.

BACKGROUND ART

A drug which is soluble in water or a solvent available for administration can be formulated into a solution with water or an appropriate solvent to prepare a medicinal product such as an injection, which can be administered. While, in the case where a drug is poorly soluble in water or a solvent available for administration, the drug can be dissolved by adding a solubilizing agent to prepare a drug solution, if available (e.g. Patent document 1), or the drug is milled into a microparticle and formulated into a suspension for administration (e.g. Patent document 2). In some cases, however, some drugs are not dissolved or insufficiently dissolved even by adding a conventional amount of a solubilizing agent, or in other cases, some solubilizing agents can make the pH value of its solution far beyond around bioavailable neutrality.

Also the method using a suspension, however, is not necessarily a universal procedure because in some cases a particle size is not sufficiently small, or in other cases a particle may be aggregated shortly after preparation or during storage. In particular, when a suspension is used for an injection, a sterilizing step such as aseptic filtration is essential, and thus it is necessary to prepare a suspension comprising a drug in the form of stable nanoparticle whose particle size is 0.2 μm (200 nm) or less available for filtration sterilization. However, it has not been realistically easy to prepare such a suspension comprising a drug in the form of the stable nanoparticle, namely it has been difficult to prepare an injectable suspension comprising a poorly-soluble drug.

In connection with recent changes of life styles, arteriosclerotic diseases such as cardiac infarction, angina, stroke, and peripheral vascular disease have been increased. Percutaneous transluminal angioplasty (referred to as "PTA" hereinafter) has been widely used as a reliable method of treating the arteriosclerotic diseases with surgical opening of narrowed or occluded parts of blood vessels, which is represented by, for example, percutaneous transluminal coronary angioplasty in a coronary of heart. PTA is a technique for recovering the blood flow, in which a balloon catheter (a tube having a balloon at its tip) or a stent is inserted from an arm or femoral artery, it is placed at a stenosis in the coronary artery, then the balloon attached at the tip is blown up to expand the stenotic blood vessel. However, the PTA-treated blood vessel is damaged such as detachment of endothelial cell and injury of elastic lamina, and the vascular intima grows because of the healing reaction in the vascular wall, thereby patients whose stenosis lesion site is opened by PTA can suffer from restenosis at a rate of about 30 to 40%.

Then, it has been suggested to try reducing the rate of restenosis by releasing a drug topically for a long time at a site for placement in a lumen, using a drug-dissolution type of a medical device for placement into a lumen wherein an anti-inflammatory agent or an inhibitor of smooth-muscle cell proliferation is supported on the surface of stent or balloon catheter which is made of metal or polymer material (Patent documents 3, 4). For example, Patent document 3 suggests a drug-eluting stent (hereinafter, abbreviated as "DES") wherein the body of a stent is coated with a biocompatible nanoparticle including a bioactive substance for the treatment, and a process of preparation thereof, which discloses a spherical crystallization technique as a process of a biocompatible nanoparticle. It is however difficult to have an effective amount of nanoparticles of a poorly-soluble drug in water such as cilostazol with the antithrombotic activity remain as the nanoparticles on the surface of a stent or balloon. Various coating methods have been tried, but any useful procedures have not been found.

[Patent document 1] WO 2009/017259
[Patent document 2] WO 2006/052018
[Patent document 3] JP-A-2007-215620
[Patent document 4] WO 2011/024831

SUMMARY OF INVENTION

Problems to be Solved by the Invention

As described above, it has been still difficult to prepare a stable liquid medicinal product such as an injection comprising a poorly-soluble drug, and in particular it has been desirable to establish a method of preparing a stable suspension (dispersed solution) comprising a drug in the form of a stable nanoparticle available for filtration sterilization, and a method for coating a stent and the like with the nanoparticle.

Means of Solving the Problems

The present inventors have found with various studies a method of preparing a stable nanoparticle of a compound which is water-insoluble or poorly water-soluble or a composition comprising the nanoparticle to achieve the present invention. In particular, the present inventors have found a novel method comprising forcing a compound which is water-insoluble or poorly water-soluble to be dissolved in water or water containing ethanol or the like at a high temperature under a high pressure, cooling the resulting solution to give a suspension comprising a uniform crystal of the compound, or followed by isolation to give the isolated crystal, and milling the resultant to prepare a dispersed solution or a solid powder comprising the compound as a nanoparticle.

The present invention relates to the following invention.

[1] A method of preparing a nanoparticle or a composition comprising a nanoparticle, comprising:
  Step (1): dissolving a compound which is water-insoluble or poorly water-soluble in water, a solvent acceptable for preparing a medicinal product or a mixture thereof at a high temperature under a high pressure;
  Step (2): cooling the resulting solution to give a suspension comprising a uniform crystal of the compound, or followed by isolation to give the isolated crystal; and
  Step (3): milling the resulting suspension or the isolated crystal.

[2] The method of [1], wherein a suspension is obtained in Step (2) and the resulting suspension is milled in Step (3) by milling-in-water procedure. In particular, it is a method of preparing a nanoparticle or a composition comprising a nanoparticle (i.e., a dispersed solution comprising a nanoparticle), comprising:
  Step (1): dissolving a compound which is water-insoluble or poorly water-soluble in water, a solvent acceptable for preparing a medicinal product or a mixture thereof at a high temperature under a high pressure;
  Step (2): cooling the resulting solution to give a suspension comprising a uniform crystal of the compound; and
  Step (3): milling the resulting suspension by milling-in-water procedure.

[3] The method of [1], wherein an isolated crystal is obtained in Step (2) and the isolated crystal is milled in Step (3) by dry- or wet-milling procedure. In particular, it is a method of preparing a nanoparticle or a composition comprising a nanoparticle (i.e., a crystal), comprising:
  Step (1): dissolving a compound which is water-insoluble or poorly water-soluble in water, a solvent acceptable for preparing a medicinal product or a mixture thereof at a high temperature under a high pressure;
  Step (2): cooling the resulting solution to give a suspension comprising a uniform crystal of the compound, followed by isolation of the crystal from the suspension; and
  Step (3): milling the isolated crystal by dry- or wet-milling procedure.

[4] The method of any one of [1] to [3], wherein the mean particle size of the nanoparticle is 200 nm or less.

[5] The method of any one of [1] to [4], wherein cyclodextrins, a dispersant, and/or a charged neutralizing agent are contained in the dissolving solvent in Step (1).

[6] The method of [5], wherein the cyclodextrins are 2-hydroxypropyl-β-cyclodextrin (HP-β-CD), and/or
  the dispersant is low-substituted methylcellulose, and/or
  the charged neutralizing agent is docusate Na.

[7] The method of any one of [1] to [6], wherein cyclodextrins, a dispersant, and/or a charged neutralizing agent are added in the milling step of Step (3).

[8] The method of [7], wherein the cyclodextrins are 2-hydroxypropyl-β-cyclodextrin (HP-β-CD), and/or
  the dispersant is low-substituted methylcellulose, and/or
  the charged neutralizing agent is docusate Na.

[9] The method of any one of [1] to [8], wherein the high temperature in Step (1) is 120° C. to 140° C.

[10] The method of any one of [1] to [9], wherein the high pressure condition in Step (1) is a pressure obtained by sealing the dissolving solvent comprising the compound in a vessel to and heating the vessel to the high temperature.

[11] The method of any one of [1] to [10], wherein the compound which is water-insoluble or poorly water-soluble is cilostazol, tranilast, indometacin, acemetacin or a pharmaceutically acceptable salt thereof.

[12] The method of [11], wherein the compound which is water-insoluble or poorly water-soluble is cilostazol or a pharmaceutically acceptable salt thereof.

[13] A nanoparticle or a composition comprising a nanoparticle which is prepared by the method of any one of [1] to [12].

[14] A nanoparticle of cilostazol or a composition comprising a nanoparticle of cilostazol which is prepared by the method comprising:
  Step (1): dissolving cilostazol in water, a solvent acceptable for preparing a medicinal product or a mixed solution thereof at a high temperature under a high pressure;
  Step (2): cooling the resulting solution to give a suspension comprising a uniform crystal of cilostazol, or followed by isolation to give the isolated crystal; and
  Step (3): milling the resulting suspension or the isolated crystal.

[15] Cilostazol which is in the form of a nanoparticle having a mean particle size of 200 nm or less.

[16] An injectable agent for treating brain infarction, comprising cilostazol which is in the form of a nanoparticle having a mean particle size of 200 nm or less.

[17] A stent or balloon catheter coated with the nanoparticle or the composition comprising a nanoparticle which is prepared by the method of any one of [1] to [12].

[18] The stent or balloon catheter of [17], wherein the compound which is water-insoluble or poorly water-soluble is cilostazol or a pharmaceutically acceptable salt thereof.

Effect of the Invention

The present invention allows for preparation of a stable aqueous injection comprising a compound even though the compound is water-insoluble or poorly water-soluble, wherein the compound particle is in the form of a nanoparticle available for filtration sterilization. The aqueous injection provided by the present invention may be freeze-dried to provide an injectable formulation for preparation at time of use.

The composition comprising a nanoparticle powder obtained by isolating the crystal in Step (2) and milling the crystal in Step (3) may be formulated into an injectable formulation for preparation at time of use and may be also applied as an embrocation.

Cilostazol in the form of a nanoparticle having a mean particle size of 200 nm or less is expected to be applied as a novel agent for treating brain infarction as shown in Test example 2 described below.

An effective amount of the composition comprising the nanoparticle of the present invention may be loaded and held on the surface of a stent or balloon. The composition of the present invention may reduce the amount of polymer which is conventionally used in coating of the medical devices to a very small amount.

BRIEF DESCRIPTION OF DRAWINGS

FIG. 1 shows micrographs before and after levigation of a cilostazol bulk powder, which is a result of Example 3.

FIG. 2 shows micrographs before and after levigation of a cilostazol crystal obtained by crystallization from water solvent, which is a result of Example 3.

FIG. 3 shows micrographs before and after levigation of a cilostazol crystal obtained by crystallization from a 50% ethanol solvent, which is a result of Example 3.

FIG. 4 shows micrographs before and after levigation of a tranilast bulk powder, which is a result of Example 3.

FIG. 5 shows micrographs before and after levigation of a tranilast crystal obtained by crystallization from water solvent, which is a result of Example 3.

FIG. 6 shows micrographs before and after levigation of a tranilast crystal obtained by crystallization from a 50% ethanol solvent, which is a result of Example 3.

FIG. 7 shows blood kinetics and parameters of cilostazol, which is a result of Test example 1. CLZ in the figure denotes cilostazol; the same can be applied hereinafter.

FIG. 8 shows the effects of intravenous administration of a dispersion solution of cilostazol nanoparticle on cerebral blood flow, which is a result of Test example 2.

FIG. 9 shows a composition of cilostazol ointment in Test example 3.

FIG. 10 shows the permeability of cilostazol ointment for in vitro rat skin and mock skin, which is a result of Test example 3.

FIG. 11 shows kinetic analysis results about in vitro rat skin permeability of cilostazol ointment, which is a result of Test example 3.

FIG. 12 shows a device applying an ointment to abdomens of rats.

FIG. 13 shows the pharmacokinetics in blood about permeability of cilostazol ointment for in vivo rat skin, which is a result of Test example 3.

FIG. 14 shows the pharmacokinetics in blood about permeability of cilostazol ointment for in vivo rat skin, which is a result of Test example 3.

FIG. 15 shows the time-dependent change of rat paw edema after administration of tranilast gel ointment, which is a result of Test example 4. Graph A shows the change of right paw and Graph B shows the change of left paw. In the figure, TRA denotes tranilast, Paw edema denotes edema of paw, and Day after adjuvant injection denotes the day after preparation of adjuvant arthritis; the same can be applied hereinafter.

FIG. 16 shows in vitro rat skin permeability of tranilast gel ointment, which is a result of Test example 4.

FIG. 17 shows the blood levels of tranilast after administration of tranilast gel ointment, which is a result of Test example 4.

FIG. 18 shows the retention levels of tranilast in the skin after administration of tranilast gel ointment, which is a result of Test example 4.

DESCRIPTION OF EMBODIMENTS

The "compound which is water-insoluble or poorly water-soluble" in the present invention is not limited as long as the compound is insoluble or poorly-soluble in water, in particular it is directed to medicinal compounds which are insoluble or poorly-soluble in water, which include, for example, cilostazol, tranilast, indometacin, acemetacin and a pharmaceutically acceptable salt thereof. Through the technique of the present invention, it is particularly expected that the oral preparation of cilostazol having antithrombotic activity is applied as an injection and the oral preparation of tranilast having anti-allergic activity is applied as an embrocation.

The "nanoparticle" in the present invention denotes a particle having a mean particle size of nano order (less than 1 μm) which is generally 200 nm or less available for filtration sterilization, preferably 100 nm or less.

The "composition comprising a nanoparticle" in the present invention denotes a composition comprising the nanoparticle, and includes, for example, a suspension comprising a nanoparticle, as well as the nanoparticle comprising an additional other pharmaceutically acceptable ingredient and a suspension thereof. The nanoparticle itself is encompassed in the composition comprising a nanoparticle.

Amongst suspensions comprising a particle, a suspension in which the particle is a nanoparticle is usually defined as a "dispersed solution" which is in the state between a suspension and a solution.

In particular, the "cilostazol which is in the form of a nanoparticle having a mean particle size of 200 nm or less" in the present invention showed higher therapeutic effects in intravenous administration to a brain ischemic model than the administration of a cilostazol solution in which cilostazol is completely dissolved, as shown in Test example 2 described below, and is expected as a novel agent for treating brain infarction alternative to tPA. The intravenous administration used herein includes administration via infusion.

The "solvent acceptable for preparing a medicinal product" used in Step (1) in the present invention is not limited as long as the solvent is a conventional solvent used in preparing medicinal products, and generally includes aqueous solvents, for example, alcohols such as ethanol, ketones such as acetone, nitriles such as acetonitrile, and ethers such as diethyl ether and THF, preferably ethanol.

The "water, a solvent acceptable for preparing a medicinal product or a mixture thereof" in Step (1) in the present invention includes preferably water or a mixture of a solvent acceptable for preparing a medicinal product and water, particularly water or a mixture of ethanol and water.

When a suspension is obtained in Step (2), the suspension is milled in Step (3), and the resulting dispersed solution is sterilized by filtration to prepare an injection, then the "water, a solvent acceptable for preparing a medicinal product or a mixed solution" is preferably water.

"Water" used herein is in the grade used in the manufacture of medicinal products and includes purified water.

The "high temperature and high pressure" in the present invention is not limited as long as the compound which is water-insoluble or poorly-soluble is dissolved in water, a solvent acceptable for preparing a medicinal product or a mixture thereof at such high temperature under such high pressure, and the compound is not decomposed, which includes, for example, 40 to 150° C., preferably 60 to 140° C., 80 to 140° C. or 100 to 140° C., more preferably 120 to 140° C., still more preferably 120 to 130° C., and the high pressure condition is preferably the pressure which is obtained by sealing a dissolving solvent comprising the compound in a vessel and heating the vessel to the high temperature.

The time required for dissolving in Step (1) in the present invention is the time until the compound is dissolved, which is usually around 10 minutes to 2 hours.

The "cooling" in Step (2) in the present invention includes cooling with water, ice water, and air, preferably cooling with water.

The "isolated crystal" in Step (2) in the present invention is directed to the crystal which is obtained on a filter after filtration of the suspension obtained in Step (2). The crystal may be also obtained by centrifugal sedimentation, followed by decantation.

As for the "milling" in Step (3) in the present invention, the suspension is milled by, for example, a milling-in-water procedure, and the isolated crystal is milled by, for example, a dry-milling procedure or a wet-milling procedure.

The milling-in-water procedure used herein is carried out with a milling instrument such as a beads mill and a microfluidizer. The dry-milling procedure is carried out with a milling instrument such as a ball mill and a roller mill. The wet-milling procedure is carried out with a milling instrument such as a ball mill and a roller mill.

The composition comprising a nanoparticle in the present invention may comprise various ingredients which may be added to a formulation besides a medicinal compound. Such ingredients include preferably a solubilizing agent, a dispersant, and a charged neutralizing agent, and specifically cyclodextrins (e.g. 2-hydroxypropyl-β-cyclodextrin) as a solubilizing agent, low-substituted methylcellulose as a dispersant, and docusate Na as a charged neutralizing agent.

The amounts of the ingredients for formulation to be added herein are not limited as long as the amounts do not affect the activity of the medicinal product and the nanoparticulation, for example, the total amount of the ingredients for formulation is 5000% (w/w) or less, preferably 10% (w/w) to 2000% (w/w), per the amount of the medicinal compound.

A method of adding the ingredients is not limited, but the addition in Step (1) is preferable for obtaining the suspension in Step (2) or the addition in Step (3) is preferable for obtaining the isolated crystal in Step (2).

The concentration of the compound in Step (1) in the present invention is not limited as long as the compound is dissolved at a high temperature under a high pressure, followed by precipitation of a crystal of the compound by cooling in Step (2), which includes 5% (w/v) or less, more preferably 2% (w/v) or less, still more preferably 2 to 0.2% (w/v).

In the present invention, a medical device such as a stent and a balloon catheter may be coated by a conventional coating technique, for example, electronic modification such as electrophoresis or atomization methods such as ultrasonic mist, spray and air brush.

EXAMPLES

The present invention is illustrated by Examples, Reference examples, and Test examples in detail below, which are not intended to limit the present invention.

Example 1. Crystallization of Poorly-Soluble Medicinal Products from Water

Poorly water-soluble medicinal products, cilostazol, tranilast, indometacin, and acemetacin, were used to prepare each suspension comprising each uniform crystal under the conditions of Table 1 (which corresponds to Step (1) to Step (2) in the method of preparation in the present invention).

In the crystallization of each medicinal product from water, each component in Table 1 was mixed under the condition of Table 1 in a 100 ml pressure-tight glass bottle with a screw cap. The mixture was entirely dissolved under heating and pressurizing, and then the mixture was shortly cooled with cold water to accelerate precipitation of a crystal of the medicinal product. The precipitated crystalline form was observed, and in all examples except for Examples 1-1, 1-4, 1-7, and 1-10, the crystal was filtered on a filter paper by suction, and then dried under reduced pressure at 60° C. to collect the crystal. A recovery rate was calculated by weighing the crystal; The recovery rate was deemed as 100% in Examples 1-1, 1-4, 1-7, and 1-10 where the crystal was not isolated.

The dried isolated crystal other than Examples 1-1, 1-4, 1-7, and 1-10 was used for preparation of a nanoparticulated medicinal product by dry-milling procedure in the following Example 2. The suspension comprising the crystal of Examples 1-1, 1-4, 1-7 or 1-10 was used for preparation of a nanoparticulated medicinal product by milling-in-water procedure in the following Example 2.

TABLE 1

| Example | Medicinal product | Content | Dispersion media | Dissolving conditions | Crystalline form | Recovery rate |
| --- | --- | --- | --- | --- | --- | --- |
| 1-1 | Cilostazol | 0.5% | 5% HP-β-CD, 0.5% low-substituted methyl cellulose, 0.1% docusate Na | 121° C., 30 min | Needle | 100% |
| 1-2 | Cilostazol | 0.5% | Purified water | 130° C., 2 hr | Needle | 98.5% |
| 1-3 | Cilostazol | 2.0% | 50% ethanol | 100° C., 20 min | Needle | 93.7% |
| 1-4 | Tranilast | 0.5% | 5% HP-β-CD, 0.5% low-substituted methyl cellulose, 0.1% docusate Na | 140° C., 2 hr | Cubic | 100% |
| 1-5 | Tranilast | 0.2% | Purified water | 150° C., 2 hr | Cubic | 97.3% |
| 1-6 | Tranilast | 2.0% | 50% ethanol | 120° C., 20 min | Cubic | 98.7% |
| 1-7 | Indometacin | 0.5% | 5% HP-β-CD, 0.5% low-substituted methyl cellulose, 0.1% docusate Na | 121° C., 30 min | Needle | 100% |
| 1-8 | Indometacin | 0.5% | Purified water | 120° C., 2 hr | Needle | 96.8% |
| 1-9 | Indometacin | 2.0% | 50% ethanol | 90° C., 20 min | Needle | 98.8% |

TABLE 1-continued

| Example | Medicinal product | Content | Dispersion media | Dissolving conditions | Crystalline form | Recovery rate |
|---|---|---|---|---|---|---|
| 1-10 | Acemetacin | 0.5% | 5% HP-β-CD, 0.5% low-substituted methyl cellulose, 0.1% docusate Na | 121° C., 30 min | Needle | 100% |
| 1-11 | Acemetacin | 0.5% | Purified water | 120° C., 2 hr | Needle | 98.9% |
| 1-12 | Acemetacin | 2.0% | 50% ethanol | 90° C., 20 min | Needle | 96.4% |

Example 2. Nanoparticulation by Milling Crystalline Medicinal Products Obtained by Crystallization from Water The medicinal product crystals of Examples 1-1 to 1-12 obtained in the above Example 1 were milled under the corresponding conditions to Examples 2-1 to 2-12 of Table 2 (which corresponds to Step (3) in the method of preparation in the present invention).

In Examples 2-1, 2-4, 2-7, and 2-10, the suspension obtained in Example 1 was milled by milling-in-water procedure, while in Examples 2-2, 2-3, 2-5, 2-6, 2-8, 2-9, 2-11, and 2-12, the dried crystal obtained in Example 1 was milled by dry-milling procedure. Dry-milling procedure was carried out after the addition of the additives in Table 2; The additives described in Table 2 for milling-in-water procedure correspond to the dispersion media used in Example 1.

Mean particle sizes and particle size distributions of the obtained nanoparticle crystals were calculated, the values of which are shown in Table 2. Recovery rates were calculated on the basis of particles filtered through a membrane filter (pore size 200 nm).

All mean particle sizes of the nanoparticulated medicinal products in Table 2 were 150 nm or less of the nanoparticle, and the obtained nanoparticle was dispersed in water, and then filtered through a membrane filter (pore size 200 nm) to give a filtrate. Every recovery rate of the drug in the filtrate was high, and recovery rates of nanoparticles prepared by milling-in-water procedure were particularly high (90% or more).

TABLE 2

| Example | Medicinal product | Content | Additive | Milling procedure | Particle size | Recovery rate (200 nm or less of particles) |
|---|---|---|---|---|---|---|
| 2-1 | Cilostazol | 0.5% | 5% HP-β-CD, 0.5% low-substituted methyl cellulose, 0.1% docusate Na | Milling-in-water procedure (bead mill, 0.1 mm zirconia beads, 5, 500 rpm, 10 min, 2° C.) | 92.2 ± 41.5 nm | 97.6% |
| 2-2 | Cilostazol | 80% | 19.9% low-substituted methyl cellulose, 0.1% docusate Na | Dry-milling procedure (zirconia automated mortar, 300 rpm, 14 hr, 22° C.) | 137 ± 87.6 nm | 87.3% |
| 2-3 | Cilostazol | 80% | 19.9% low-substituted methyl cellulose, 0.1% docusate Na | Dry-milling procedure (zirconia automated mortar, 300 rpm, 14 hr, 22° C.) | 119 ± 55.7 nm | 92.0% |
| 2-4 | Tranilast | 0.5% | 5% HP-β-CD, 0.5% low-substituted methyl cellulose, 0.1% docusate Na | Milling-in-water procedure (bead mill, 0.1 mm zirconia beads, 5, 500 rpm, 10 min, 2° C.) | 84.7 ± 31.2 nm | 99.2% |
| 2-5 | Tranilast | 80% | 19.9% low-substituted methyl cellulose, 0.1% docusate Na | Dry-milling procedure (zirconia automated mortar, 300 rpm, 14 hr, 22° C.) | 103 ± 47.8 nm | 94.6% |
| 2-6 | Tranilast | 80% | 19.9% low-substituted methyl cellulose, 0.1% docusate Na | Dry-milling procedure (zirconia automated mortar, 300 rpm, 14 hr, 22° C.) | 96.9 ± 40.8 nm | 97.7% |
| 2-7 | Indometacin | 0.5% | 5% HP-β-CD, 0.5% low-substituted methyl cellulose, 0.1% docusate Na | Milling-in-water procedure (bead mill, 0.1 mm zirconia beads, 5, 500 rpm, 10 min, 2° C.) | 111 ± 44.7 nm | 96.4% |

TABLE 2-continued

| Example | Medicinal product | Content | Additive | Milling procedure | Particle size | Recovery rate (200 nm or less of particles) |
|---|---|---|---|---|---|---|
| 2-8 | Indometacin | 80% | 19.9% low-substituted methyl cellulose, 0.1% docusate Na | Dry-milling procedure (zirconia automated mortar, 300 rpm, 14 hr, 22° C.) | 127 ± 68.7 nm | 86.5% |
| 2-9 | Indometacin | 80% | 19.9% low-substituted methyl cellulose, 0.1% docusate Na | Dry-milling procedure (zirconia automated mortar, 300 rpm, 14 hr, 22° C.) | 102 ± 44.2 nm | 90.6% |
| 2-10 | Acemetacin | 0.5% | 5% HP-β-CD, 0.5% low-substituted methyl cellulose, 0.1% docusate Na | Milling-in-water procedure (bead mill, 0.1 mm zirconia beads, 5, 500 rpm, 10 min, 2° C.) | 90.2 ± 55.4 nm | 96.5% |
| 2-11 | Acemetacin | 80% | 19.9% low-substituted methyl cellulose, 0.1% docusate Na | Dry-milling procedure (zirconia automated mortar, 300 rpm, 14 hr, 22° C.) | 147 ± 95.7 nm | 78.5% |
| 2-12 | Acemetacin | 80% | 19.9% low-substituted methyl cellulose, 0.1% docusate Na | Dry-milling procedure (zirconia automated mortar, 300 rpm, 14 hr, 22° C.) | 127 ± 74.2 nm | 91.7% |

Comparative Example 1. Particles Milled without Crystallization from Water

To examine the effect of the crystallization-from-water in the present invention, medicinal product bulk powders (without being subjected to crystallization) were milled by milling-in-water procedure or dry-milling procedure without crystallization-from-water to prepare particles, and the particle size of the particles and recovery rates were determined. The conditions of milling, and the particle sizes and recovery rates of the obtained particles are shown in Table 3.

The particle sizes were big, the variability of the particle sizes was wide, and the recovery rates of nanoparticles with 200 nm or less were low (2 to 30%) in Comparative examples 3-1 to 3-8 milled without crystallization-from-water, compared to the particle size in each Example of the above Example 2 which was nanoparticulated in two steps of crystallization from water and milling.

TABLE 3

| Comparative Example | Medicinal product | Content | Additive | Milling procedure | Particle size | Recovery rate (200 nm or less of particles) |
|---|---|---|---|---|---|---|
| 3-1 | Cilostazol bulk powder | 0.5% | 5% HP-β-CD, 0.5% low-substituted methyl cellulose, 0.1% docusate Na | Milling-in-water procedure (bead mill, 0.1 mm zirconia beads, 5, 500 rpm, 10 min, 2° C.) | 193 ± 105 nm | 30.7% |
| 3-2 | Cilostazol bulk powder | 80% | 19.9% low-substituted methyl cellulose, 0.1% docusate Na | Dry-milling procedure (zirconia automated mortar, 300 rpm, 14 hr, 22° C.) | 272 ± 185 nm | 8.7% |
| 3-3 | Tranilast bulk powder | 0.5% | 5% HP-β-CD, 0.5% low-substituted methyl cellulose, 0.1% docusate Na | Milling-in-water procedure (bead mill, 0.1 mm zirconia beads, 5, 500 rpm, 10 min, 2° C.) | 257 ± 117 nm | 20.8% |
| 3-4 | Tranilast bulk powder | 80% | 19.9% low-substituted methyl cellulose, 0.1% docusate Na | Dry-milling procedure (zirconia automated mortar, 300 rpm, 14 hr, 22° C.) | 214 ± 181 nm | 13.3% |
| 3-5 | Indometacin bulk powder | 0.5% | 5% HP-β-CD, 0.5% low-substituted methyl cellulose, 0.1% docusate Na | Milling-in-water procedure (bead mill, 0.1 mm zirconia beads, 5, 500 rpm, 10 min, 2° C.) | 317 ± 185 nm | 2.1% |

TABLE 3-continued

| Comparative Example | Medicinal product | Content | Additive | Milling procedure | Particle size | Recovery rate (200 nm or less of particles) |
|---|---|---|---|---|---|---|
| 3-6 | Indometacin bulk powder | 80% | 19.9% low-substituted methyl cellulose, 0.1% docusate Na | Dry-milling procedure (zirconia automated mortar, 300 rpm, 14 hr, 22° C.) | 288 ± 147 nm | 5.5% |
| 3-7 | Acemetacin bulk powder | 0.5% | 5% HP-β-CD, 0.5% low-substituted methyl cellulose, 0.1% docusate Na | Milling-in-water procedure (bead mill, 0.1 mm zirconia beads, 5, 500 rpm, 10 min, 2° C.) | 267 ± 147 nm | 10.9% |
| 3-8 | Acemetacin bulk powder | 80% | 19.9% low-substituted methyl cellulose, 0.1% docusate Na | Dry-milling procedure (zirconia automated mortar, 300 rpm, 14 hr, 22° C.) | 227 ± 113 nm | 17.2% |

Example 3. Changes of Milling Properties of Cilostazol and Tranilast by Recrystallization Each 1 g of cilostazol (CLZ) bulk powder, CLZ recrystals from water (the crystals obtained in Example 1-2), CLZ recrystals from 50% ethanol (the crystals obtained in Example 1-3), tranilast (TRA) bulk powder, TRA recrystal from water (the crystals obtained in Example 1-5), and TRA recrystal from 50% ethanol (the crystals obtained in Example 1-6) were measured to be added to an agate mortar, followed by manual levigation for 30 minutes at room temperature to be observed with a scanning microscope (where a magnification was at 100-folds respectively, and the actual size was shown in scale). The results are shown in FIG. 1 to FIG. 6. In any cases, the recrystallized crystals were more finely-milled ones.

Test Example 1. Pharmacokinetics in Blood after Intravenous Administration of a Dispersion Solution Comprising Cilostazol Nanoparticle The following experiments were carried out to study the differences of blood kinetics between when a dispersion solution comprising cilostazol nanoparticle is intravenously administered and when a cilostazol solution wherein cilostazol is completely dissolved with HP-β-CD is intravenously administered.

The dispersion solution comprising cilostazol nanoparticle (0.5%) obtained as Example 2-1 in Table 2 and cilostazol solution (0.05% in 10% HP-β-CD solution) were sterilized by filtration (0.2 μm pore size, membrane filter) to be injected to femoral veins of Wistar male rats (weight: about 200 g) in an amount of 0.6 mg/kg (as cilostazol). Blood was temporally collected from cervical veins and pharmacokinetics in blood was analyzed.

The resulting cilostazol levels in the blood are shown in FIG. 7. Both cilostazol nanoparticles and cilostazol solution showed a biphasic dissipation behavior. No significant difference was recognized between them in kinetic parameters analyzed by the 2-compartment model (FIG. 7), and the dispersion solution comprising nanoparticles was approximately comparable to the solution in terms of pharmacokinetics of cilostazol in blood.

Test Example 2. Therapeutic Effects on Brain Infarction after Intravenous Administration of a Dispersion Solution Comprising Cilostazol Nanoparticle In order to test the antithrombotic activity of cilostazol in the present invention, a dispersion solution comprising cilostazol nanoparticle (0.5%) of Test example 1 and a cilostazol solution (0.05% in 10% HP-β-CD solution) were intravenously administered to the following rat brain ischemic model to study the therapeutic effects of them comparing each other.

(Preparation of Rat Forebrain Ischemic Model)

Rats are anesthetized with somnopentyl (29.8 mg/kg, i.p.), bilateral common carotid arteries thereof are exposed and the blood flow thereof is blocked with artery clamps. After 15 minutes reperfusion is implemented, and after 20 minutes, a dispersion solution comprising cilostazol nanoparticle and a cilostazol solution are intravenously administered (while femoral veins are exposed). The abdomen is sutured, and the cerebral blood flow is measured after 24 hours.

(Measurement of Cerebral Blood Flow)

The test rats are anesthetized with urethane (1.2 mg/kg, i.p.), and heads are incised and a hole is made in cranial bone. The cerebral blood flow is measured with a laser tissue blood flowmeter OMEGAFLO FLO-N1 (manufactured by Omegawave, Inc.), and the blood flow, blood volume, and blood velocity are calculated from the following equations.

$$\text{Blood flow} = k_1 \int \omega P(\omega) d\omega / I^2$$

$$\text{Blood volume} = In[1 - k_2 \int P(\omega) d\omega)] / I^2$$

$$\text{Blood velocity} = k_3 [\text{blood flow/blood volume}]$$

$k_1$-$k_3$: Proportional constant
$\omega$: Angular frequency ($2\pi f$)
$P(\omega)$: Power spectrum of signal
I: Amount of light received (Results)

The results are shown in FIG. 8. The administration of a dispersion solution comprising a nanoparticle showed higher therapeutic effects in brain ischemic model rats rather than that of a cilostazol solution which higher therapeutic effects were expected, and according to the result of FIG. 8, the improvement in cerebral blood flow and cerebral blood volume were recognized only in the intravenous administration of a dispersion solution comprising cilostazol nanoparticle in 0.6 mg/kg of doses.

Test Example 3. Pharmacokinetics in Blood after Percutaneous Application of a Gel Ointment Comprising Cilostazol Nanoparticle The following experiments were carried out to compare blood kinetics in percutaneous application of an aqueous gel ointment comprising cilostazol nanoparticle to that in a gel ointment comprising cilostazol bulk powder.

An aqueous gel ointment comprising cilostazol nanoparticle, a PEG ointment, and a gel ointment comprising cilostazol bulk powder were prepared according to the composition shown in FIG. 9.

In Vitro Rat-Skin and Mock-Skin Permeation Experiment
(Test Method)

7-Week old Wistar male rats were pretreated for the experiment by removing their abdominal hairs. The next day, abdominal skins (diameter 3.5 cm) of the unhaired parts were enucleated to be set in a diffusive cell. Separately, rubber sheets (thickness 75 μm) were used as mock skins for the experiment instead of rat skins. The bottom part of the cell was filled with phosphate buffer (pH 7.2), and the ointment (0.3 g) was applied to the horny layer part in the upper part of the cell, followed by sealing with aluminum foils. The bottom part of the cell was stirred with a rotator while maintaining the temperature at 37° C. with a constant-temperature bath, and samples (100 μl) were collected from the bottom part of the cell with time after 0, 2, 4, 6, 8, 10, 24, 28, 32, and 50 hours with supplement of the same amount of buffer. Cilostazol contents in the samples were measured with HPLC.

The obtained data were applied to the following diffusion formulae (1) and (2) to calculate 5 kinetic parameters.

$$J_c = \frac{Q}{A(t-\tau)} = \frac{D \cdot K_m \cdot C_c}{\delta} = K_p \cdot C_c \quad (1)$$

$$D = \frac{\delta^2}{6\tau} \quad (2)$$

$J_c$ denotes the drug permeability rate, $K_m$ denotes the partition coefficient of skin/formulation, D denotes the diffusion coefficient in the skin, τ denotes the ragtime, δ denotes the thickness (average 0.071 cm) of the skin, A denotes the effective area (2.01 cm$^2$) of the skin used, Q denotes the cumulative drug amount permeated the bottom part of the cell for t hours, and $C_c$ denotes the cilostazol level in the cilostazol ointment formulation. The skin permeability coefficient $K_p$ was calculated from $J_c/C_c$.

(Measurement of Cilostazol Levels with HPLC)

The sample (10 μL) and a methylphenytoin solution (15 μg/mL, 90 μL) as an internal standard were mixed, stirred, and then centrifuged (4° C., 20 min, 15000 rpm). The measurement was carried out with the resulting supernatant. A HPLC composed of a high-performance liquid chromatograph LC-10AD (Shimadzu Corporation), a chromatography chamber CTO-6A maintained at 35° C., and Inertsil ODS-3 (2.1×50 mm, GL Sciences Inc.) was previously run with a mobile phase of CH$_3$CN/MeOH/H$_2$O=35/15/50 (v/v/v). The flow rate of the mobile phase was 0.25 mL/min, the sample injection amount was 4 μL, and the sample was automatically injected into the column with an auto injector SIL-9A. Cilostazol was detected with a flow-through cell detector SPD-10A at the absorption wavelength of 254 nm and recorded with a chromatograph EPC-500.

(Results)

The results are shown in FIG. 10 and FIG. 11. An aqueous gel ointment and a PEG ointment which comprise cilostazol nanoparticle showed higher rat skin permeability of cilostazol than a similar gel ointment comprising bulk powders of cilostazol. Any ointments did not permeate a mock skin having a silicone rubber with the thickness of 75 μm. That shows that the skin permeation of cilostazol nanoparticle is not based on simple diffusion of drugs but based on transcytosis of cells constituting biomembranes.

In Vivo Transdermal Absorption Experiment

The pharmacokinetics of cilostazol in blood after the percutaneous application was evaluated in vivo.

(Test Method)

7-Week old Wistar male rats were pretreated for the experiment by removing their abdominal hairs and cannulating their cervical veins (the cannulation procedure of cervical veins is described below). The next day, the ointment (0.22 g) was applied to the unhaired parts with the device shown in FIG. 12. The device was prepared with a silicone gum sheet and an aluminum foil (manufactured by Nippon Foil Mfg. Co., Ltd.), said silicone gum sheet had been cut in a circle with the outer diameter of 24 mm and the internal diameter of 18 mm. Blood was collected from the cervical veins 0, 2, 4, 6, 8, 10, 12, 24, 28, 32, and 50 hours after the ointment application. The collected blood was centrifuged (4° C., 15000 rpm, 20 min) to collect a supernatant, and the supernatant was measured under the HPLC condition of the in vitro experiment mentioned above.

(Cannulation of Cervical Veins)

Blood was collected from rats with cannulation of cervical veins. Rats were anesthetized with somnopentyl (30 mg/kg, i.p.) to keep them in the supine position, make an incision in the skin of the cervical part at about 1.5 cm on the right side, and separate muscles with tweezers to exteriorize external cervical veins. A Phycon tube (SH No. 00) filled with heparin (10 IU/mL heparin sodium injection) was then penetrated subcutaneously from the back of the neck through outside the body to connect to a syringe barrel. The external cervical veins were then bound with two sutures, one of which on the side of the heart was pulled to fix and stop the blood flow and the other of which on the side of the cervical part was strongly ligated. The exposed blood vessel was made a cut line with scissors and the Phycon tube was inserted about 3 cm therein. After the blood flow in the tube was observed with the syringe barrel, the suture on the side of the heart was ligated. The incision site was then sutured. The change of the blood levels after the ointment application was evaluated without anesthesia. The blood was collected with time. About 0.2 mL of the collected blood was set in a 0.5 mL microtube, and centrifuged with a centrifuge (MX-200 TOMY) under the condition of 4° C., 20 min, and 15000 rpm. The resulting supernatant was analyzed about the drug quantitation with HPLC.

The results are shown in FIGS. 13 and 14. It was observed that the blood levels of cilostazol and the percutaneous absorption rates were higher in an aqueous gel ointment and a PEG ointment which comprise cilostazol nanoparticle. In particular, the aqueous gel ointment showed higher absorption velocity (ka) and absorption rate. Cilostazol however could not be observed in blood for a gel ointment comprising cilostazol bulk powder.

Test Example 4. Preparation of a Gel Ointment Comprising Tranilast Nanoparticle and Therapeutic Effect of the Same on Adjuvant Arthritis Rats in Percutaneous Application The therapeutic effect of tranilast on the anti-allergic activity was studied to compare the percutaneous administration of an aqueous gel ointment comprising tranilast nanoparticle with that of an aqueous gel ointment comprising tranilast bulk powder to the following rat rheumatoid arthritis model.

(Preparation of Rat Rheumatoid Arthritis Model)

Seven-week old Dark Agouti (DA) rats were used in the experiment. DA rats were anesthetized by inhalation, and then an adjuvant of 50 µL each was injected to their right hind limbs and tails to prepare adjuvant-induced rheumatoid arthritis (AA) rats. The adjuvant was prepared as follows. Killed *Mycobacterium butyricum* (100 mg; DIFCO LABORATORIES) was set in an agate mortar to be grinded, and then thereto was added Bayol F (manufactured by Wako; 10 mL) in small amounts. The mixture was further grinded with being stirred. The resulting suspension was divided in 500 µL each in Prastic Cryogenic Vials (manufactured by IWAKI & Co., Ltd.). The vials were covered with an aluminum foil and sterilized with an autoclave (120° C., 15 min), and then stored in a refrigerator until use.

(Preparation of an Aqueous Gel Ointment Comprising Tranilast Nanoparticle and an Aqueous Gel Ointment Comprising Tranilast Bulk Powder)

Carbopol 934 (Registered trade mark, carboxyvinyl polymer) was dissolved in purified water to let it stand for 1 hour, and was then neutralized with the addition of 5% ammonia water with being stirred. Thereto was added a dispersion solution comprising tranilast nanoparticle with an optional addition of purified water to prepare an aqueous gel ointment comprising tranilast nanoparticle.

An aqueous gel ointment comprising tranilast bulk powder was prepared according to the above procedure with a suspension of tranilast bulk powder instead of the dispersion solution comprising tranilast nanoparticle.

Measurement of Rat Edema (Test Method)

The ointment (0.3 g) was applied only to the right limb at 9:00 every morning once a day from 14 days after the adjuvant administration. The limb volumes were measured to show the extent of inflammation in rat joints. The limb volumes were measured with a solution which was prepared by dissolving a teaspoon of sodium carboxymethylcellulose in purified water (400 mL) and stained with 3 or 4 powders of Evans Blue. The limbs were soaked in this solution to measure the change of edema.

In Vitro Percutaneous Permeation Experiment (Test Method)

7-Week old Wistar male rats were pretreated for the experiment by removing their abdominal hairs. The next day, abdominal skins (diameter of 3.5 cm) of the unhaired parts were enucleated to be set in a diffusive cell. The bottom part of the cell was filled with phosphate buffer (pH 7.2), and the ointment (0.3 g) was applied to the horny layer part in the upper part of the cell, followed by sealing with aluminum foils. The bottom part of the cell was stirred with a rotator while maintaining the temperature at 37° C. with a constant-temperature bath, and samples (100 µl) were collected from the bottom part of the cell with supplement of the same amount of buffer with time. Tranilast contents in the samples were measured with HPLC.

(Measurement of TRA Levels with HPLC)

The sample (10 µL) and ethyl p-oxybenzoate (3 µg/mL; 90 µL) as an internal standard were mixed, stirred, and then centrifuged (4° C., 20 min, 15000 rpm). The measurement was carried out with the resulting supernatant. A HPLC composed of a high-performance liquid chromatograph LC-10AD (Shimadzu Corporation), a chromatography chamber CTO-6A maintained at 35° C., and Inertsil ODS-3 (2.1×50 mm, GL Sciences Inc.) was previously run with a mobile phase of ($CH_3CN$/50 mM ammonium acetate=20/80). The flow rate of the mobile phase was 0.25 mL/min, the sample injection amount was 4 µL, and the sample was automatically injected into the column with an auto injector SIL-9A. TRA was detected with a flow-through cell detector SPD-10A at the absorption wavelength of 230 nm and recorded with a chromatograph EPC-500.

In Vivo Transdermal Absorption Experiment (Test Method)

7-Week old Wistar male rats were pretreated for the experiment by removing their abdominal hairs and cannulating the cervical veins (the cannulation procedure of cervical veins is described below). The next day, the ointment (0.3 g) was applied to the unhaired parts with the device shown in FIG. 12. The device was prepared with a silicone gum sheet and an aluminum foil (manufactured by Nippon Foil Mfg. Co., Ltd.), said silicone gum sheet had been cut in a circle with the outer diameter of 24 mm and the internal diameter of 18 mm. Blood was collected from cervical veins with time over 0 to 12 hours after the ointment application. The collected blood was centrifuged (4° C., 15000 rpm, 20 min) to collect a supernatant, and the supernatant was measured under the HPLC condition of the in vitro experiment mentioned above.

(Cannulation of Cervical Veins)

Blood was collected from rats by cannulation of cervical veins. Rats were anesthetized with somnopentyl (30 mg/kg, i.p.) to keep them in the supine position, make an incision in the skin of the cervical part at about 1.5 cm on the right side, and separate muscles with tweezers to exteriorize external cervical veins. A Phycon tube (SH No. 00) filled with heparin (10 IU/mL heparin sodium injection) was then penetrated subcutaneously from the back of the neck through outside the body to connect to a syringe barrel. The external cervical veins were then bound with two sutures, one of which on the side of the heart was pulled to fix and stop the blood flow and the other of which on the side of the cervical part was strongly ligated. The exposed blood vessel was made a cut line with scissors and the Phycon tube was inserted about 3 cm therein. After the blood flow in the tube was observed with the syringe barrel, the suture on the side of the heart was ligated. The incision site was then sutured. The change of the blood levels after the ointment application was evaluated without anesthesia. The blood was collected with time. About 0.2 mL of the collected blood was set in a 0.5 mL microtube, and centrifuged with a centrifuge (MX-200 TOMY) under the condition of 4° C., 20 min, and 15000 rpm. The resulting supernatant was analyzed about the drug quantitation with HPLC.

In Vivo Skin Retention Experiment (Test Method)

7-Week old Wistar male rats were pretreated for the experiment by removing their abdominal hairs. The next day, the ointment (0.3 g) was applied to the unhaired parts with the device shown below. The device was prepared with a silicone gum sheet and an aluminum foil (manufactured by Nippon Foil Mfg. Co., Ltd.), said silicone gum sheet had been cut in a circle with the outer diameter of 24 mm and the internal diameter of 18 mm. Twelve hours after the ointment application, the skin area to which a tranilast gel ointment or a tranilast nano gel ointment was applied was wiped five times with an absorbent cotton containing saline to exfoliate cuticles. The skin without containing fat was then exfoliated. The resulting skin was set in a 0.5 mL microtube and homogenized with purified water (500 μL). The homogenized solution was then centrifuged with a centrifuge under the condition of 4° C., 15000 rpm, and 20 min to give a supernatant, and the supernatant was measured under the HPLC condition of the in vitro experiment mentioned above.

(Results)

FIG. 15 shows the time-dependent change of rat limb edema after administration, FIG. 16 shows the in vitro rat skin permeability of a tranilast gel ointment after administration, FIG. 17 shows the blood level of tranilast after administration, and FIG. 18 shows the retention level of tranilast to skins after administration.

The result of FIG. 15 shows that the percutaneous application of the gel ointment comprising tranilast nanoparticle strongly inhibited edema in rat adjuvant arthritis of a rheumatoid arthritis model. That effect was not observed in a similar ointment comprising tranilast bulk powder as a comparison.

The result of FIG. 16 shows that in a gel ointment comprising 0.35 to 0.75% of tranilast, the ointment comprising the dispersed nanoparticle had a better permeability in each content than the bulk powder suspension.

The result of FIG. 17 shows that the aqueous gel ointment comprising tranilast nanoparticle had a significantly higher transitivity in blood than a similar gel ointment comprising tranilast bulk powder.

The result of FIG. 18 shows that the aqueous gel ointment comprising tranilast bulk powder had a higher tranilast level in the skin than the aqueous gel ointment comprising tranilast nanoparticle.

Dose-response correlation was recognized in the drug absorption from the rat skin after application of the gel ointment comprising tranilast nanoparticle.

The invention claimed is:

1. A method of preparing a nanoparticle or a composition comprising a nanoparticle, comprising:
   Step (1): dissolving a compound which is water-insoluble or poorly water-soluble in (i) water, (ii) a solvent acceptable for preparing a medicinal product or (iii) a mixture thereof at a temperature of 100 to 140° C. in a sealed vessel;
   Step (2): cooling the resulting solution to give a suspension comprising a uniform crystal of the compound, or followed by isolation to give the isolated crystal; and
   Step (3): milling the resulting suspension or the isolated crystal,
   wherein the compound is cilostazol or a pharmaceutically acceptable salt thereof.

2. The method of claim 1, wherein a suspension is obtained in Step (2) and the resulting suspension is milled in Step (3) by milling-in-water procedure.

3. The method of claim 1, wherein an isolated crystal is obtained in Step (2) and the isolated crystal is milled in Step (3) by dry- or wet-milling procedure.

4. The method of claim 1, wherein the mean particle size of the nanoparticle is 200 nm or less.

5. The method of claim 1, wherein cyclodextrins, a dispersant, and/or a charged neutralizing agent are contained in the dissolving solvent in Step (1).

6. The method of claim 5, wherein the cyclodextrins are 2-hydroxypropyl-β-cyclodextrin (HP-β-CD), and/or
   the dispersant is low-substituted methylcellulose, and/or
   the charged neutralizing agent is docusate Na.

7. The method of claim 1, wherein cyclodextrins, a dispersant, and/or a charged neutralizing agent are added in the milling step of Step (3).

8. The method of claim 7, wherein the cyclodextrins are 2-hydroxypropyl-β-cyclodextrin (HP-β-CD), and/or
   the dispersant is low-substituted methylcellulose, and/or
   the charged neutralizing agent is docusate Na.

9. The method of claim 1, wherein the temperature in Step (1) is 120° C. to 140° C.

10. A nanoparticle or a composition comprising a nanoparticle which is prepared by the method of claim 1.

11. A stent or balloon catheter coated with the nanoparticle or the composition comprising a nanoparticle which is prepared by the method of claim 1.

12. The stent or balloon catheter of claim 11, wherein the compound which is water-insoluble or poorly water-soluble is cilostazol or a pharmaceutically acceptable salt thereof.

13. The method of claim 1, wherein the temperature in Step (1) is 100° C. to 130° C.

* * * * *